(12) United States Patent
Yan et al.

(10) Patent No.: US 12,023,496 B2
(45) Date of Patent: Jul. 2, 2024

(54) CLOSED-LOOP ADAPTIVE AC STIMULATION NEURAL NETWORK REGULATION METHOD AND SYSTEM

(71) Applicant: Beijing Institute University, Beijing (CN)

(72) Inventors: Tianyi Yan, Beijing (CN); Zhongyan Shi, Beijing (CN); Zilong Yan, Beijing (CN); Bo Jiang, Beijing (CN); Duanduan Chen, Beijing (CN); Tiantian Liu, Beijing (CN); Jiangtao Zhang, Beijing (CN); Guangying Pei, Beijing (CN); Jian Zhang, Beijing (CN); Jinglong Wu, Beijing (CN)

(73) Assignee: BEIJING INSTITUTE UNIVERSITY, Beijing (CN)

(*) Notice: Subject to any disclaimer, the term of this patent is extended or adjusted under 35 U.S.C. 154(b) by 0 days.

(21) Appl. No.: 18/262,186

(22) PCT Filed: Jun. 13, 2022

(86) PCT No.: PCT/CN2022/098478
§ 371 (c)(1),
(2) Date: Jul. 19, 2023

(87) PCT Pub. No.: WO2023/201863
PCT Pub. Date: Oct. 26, 2023

(65) Prior Publication Data
US 2024/0042204 A1  Feb. 8, 2024

(30) Foreign Application Priority Data
Apr. 18, 2022 (CN) .......................... 202210406598.9

(51) Int. Cl.
*A61N 1/36* (2006.01)
*A61B 5/00* (2006.01)
*A61B 5/369* (2021.01)

(52) U.S. Cl.
CPC .......... *A61N 1/36031* (2017.08); *A61B 5/369* (2021.01); *A61B 5/4836* (2013.01)

(58) Field of Classification Search
CPC .... A61N 1/36031; A61B 5/369; A61B 5/4836
See application file for complete search history.

(56) References Cited

FOREIGN PATENT DOCUMENTS

| CN | 109656365 A | 4/2019 |
|----|-------------|--------|
| CN | 113180693 A | 7/2021 |

OTHER PUBLICATIONS

PCT/CN2022/098478—International Search Report and Written Opinion, dated Jan. 12, 2023, 18 pages. (with English translation).

*Primary Examiner* — Amanda K Hulbert
*Assistant Examiner* — Philip C Edwards
(74) *Attorney, Agent, or Firm* — Getech Law LLC; Jun Ye

(57) ABSTRACT

This invention relates to a closed-loop adaptive AC stimulation neural network control method and system, involving the technical field of AC stimulation neural regulation. This system is composed of an individualized navigation module, AC stimulation module, EEG acquisition module and adaptive coupling module. After the magnetic resonance image and functional magnetic resonance image of the regulation object are input into the individualized navigation module, the functional connectivity network is generated to finalize regulatory targets. The position of stimulating electrodes and the magnitude of the stimulating current are determined according to the target to be regulated. The stimulating (Continued)

frequency is determined according to the EEG of the regulation object and then input into the AC stimulation module for regulation.

5 Claims, 4 Drawing Sheets

CLOSED-LOOP ADAPTIVE AC STIMULATION NEURAL NETWORK REGULATION METHOD AND SYSTEM

CROSS REFERENCE OF RELATED APPLICATION

The present application is a 371 of international patent application PCT/CN2022/098478, filed Jun. 13, 2022, which claims priority to Chinese Patent Application No. 2022104065989, filed on Apr. 18, 2022. The contents of the applications are incorporated herein by reference in their entireties.

TECHNICAL FIELD

This invention belongs to the technical field of neural networks and particularly relates to a closed-loop adaptive AC stimulation neural network control method and system.

BACKGROUND ART

Brain network synchronization is the basis of human cognition. The electrophysiological rhythm synchronization of the brain realizes the effective communication between brain networks. Typical brain network rhythms include: $\delta$(1-4 Hz), $\theta$(4-7 Hz), $\alpha$(8-13 Hz), $\beta$(14-30 Hz) and $\gamma$(31-90 Hz). Each rhythm has its own characteristics and the cognitive function associated with it. For instance, the most prominent cognitive relevance of $\delta$ rhythm activity is detecting the targets in a series of interfering substances or stimuli. $\theta$ rhythm is most commonly associated with the memory process. Some studies have shown that $\theta$ rhythm reflects communication with the hippocampus. Many low frequency rhythms are associated with functional inhibition. However, the high-frequency $\gamma$ rhythm is deemed to reflect the activation of the cerebral cortex and appears at high levels of concentration or in working memory activity in normal people. The synchronism of brain network rhythms promotes the coordination between functional networks. The communication between brain networks will be interrupted in case of brain rhythm disturbance, resulting in a series of neuropsychiatric disorders. Therefore, the regulation of brain network rhythms and the promotion of brain network phase synchronization are of great significance for the improvement of some neuropsychiatric disorders.

For the synchronous regulation of brain network rhythms, transcranial alternating current stimulation (TACS) is a highly effective non-invasive neuroregulatory technique. Regulating brain network rhythms by applying a low-intensity sinusoidal alternating current (the current is generally lower than 2 mA; and the frequency is generally lower than 100 Hz). This technique has some applications in cognitive neuroscience and clinical practices and has the advantages of low cost, high safety and few side effects. Relevant studies have shown that the field strength required for neural regulation should be greater than 0.2V/m. Therefore, the effective focus is required for the stimulation targets. TACS may regulate non-target positions during the regulation due to its poor focus. High-density transcranial alternating current stimulation (HD-TACS) effectively solves this problem, so that the regulated region is focused on the region enclosed by electrodes. However, HD-TACS has a problem that only a single region can be regulated. Therefore, for the whole neural network, multi-target regulation is required to realize the optimal regulatory effect. The distribution of electric fields in the brain differs greatly due to the existence of individual differences. Therefore, specific arrangements of stimulation electrodes should be customized for individualized brain networks. In order to enable external stimuli to effectively regulate brain network rhythms, external stimuli should be coupled to the real-time brain rhythm state.

SUMMARY

This invention relates to a closed-loop adaptive AC stimulation neural network regulation method that is aimed at solving the above problems and realizing the effective regulation of neural network rhythms.

This invention is realized by a closed-loop adaptive AC stimulation neural network regulation method and includes the following steps:

S1: obtain the EEG image data of the regulation data, build head models and functional connectivity network, identify multiple targets for regulation and configure the current parameters of electrical stimulation output at each target according to the simulation and optimization results;

S2: electrically stimulate each target according to current parameters, measure the impedance in real time during the stimulation, and regulate the current output;

S3: perform EEG acquisition on each target after stimulation, and pre-process the data acquired;

S4: for the pre-processed data, use zero phase shift FIR filter for zero phase shift band filtering for specific band range according to the set time window; use the AR model for phase prediction for the filtered signal; carry out FFT power spectrum analysis to obtain the main frequency;

S5: regulate current parameters according to the predicted phase and main frequency, and repeat S2-S4 to realize the closed-loop neural network regulation.

Ulteriorly, S1 specifically includes: building a 5-layer head model composed of the scalp, skull, cerebrospinal fluid, gray matter, white matter with MRI data and simnibs software; generating a functional connectivity network with fMRI data and GRETNA kit.

Further, S1 also includes: comparing the fMRI and EEG data with the Brain functional network and rhythm of normal people to obtain the abnormal region and rhythm that are the target of electrical stimulation and the frequency of regulation.

Ulteriorly, in S1, the position of the stimulating electrode and the magnitude of the stimulating current are determined by optimizing multiple HD-TACS, specifically including: stimulate multiple targets with multiple electrodes to obtain the position of multiple stimulating electrodes by the least square method and based on the international 10/10 EEG system; perform parallel optimization by single electrode superposition method according to the superposition of electric field and the linear relation of current, after setting the common reference electrode, calculate the unit current of each electrode, realize the focus at the target position within the limited safe current range under the following evaluation conditions: the electric field in the target position in the region surrounded by the peripheral electrode is the largest; and the ratio of the electric field inside and outside the target is the smallest; change the current at the electrodes in each group to make the sum of the two conditions the minimum.

Further, the pre-processing steps in S3 include: removing the noise and artifacts from the data acquired by ASR.

This invention also relates to a closed-loop adaptive AC stimulation neural network regulation system that is aimed at solving the above problems and realizing the effective regulation of neural network rhythms.

A closed-loop adaptive AC stimulation neural network regulation system, including:

The individualized navigation module builds the head model and functional connectivity network with the image data of the regulation object, identifies the multiple targets to be regulated, and optimizes the position of stimulating electrode and current by means of multiple HD-TACS;

The AC stimulation module electrically stimulates multiple targets and configures electrode parameters through electrode position and current parameters, and regulates the output current in real time combined with impedance detection;

The EEG acquisition module performs EEG acquisition at electrically stimulated targets and pre-processes EEG;

The adaptive coupling module analyzes and processes the pre-processed EEG, predicts the phase, re-sets the stimulating current and frequency of electrical stimulation and realizes the closed-loop neural network regulation.

Further, the HD-TACS is composed of four peripheral electrodes and one central electrode.

Ulteriorly, the AC stimulation module is composed of a current calculation module, current generation module, current output module and impedance detection module. The current calculation module is used to calculate the current of each stimulating electrode according to the position information received. The current generation module is used to generate the stimulating waveform of each stimulating electrode based on the current calculated. The current output module is used to output electrical stimulation current and acquire EEG voltage. The impedance detection module is used to collect the current signal of electrodes and calculate the real-time resistance value.

Further, the current output module is equipped with a limit-voltage protection circuit with a limited voltage of 24V.

Ulteriorly, the current output module has 8 channels, each of which is composed of 5 electrodes, 4 for negative input and 1 for positive output.

Compared with existing techniques, the beneficial effect of this invention is: this invention discloses a closed-loop adaptive AC stimulation neural network regulation method and system. After the magnetic resonance image and functional magnetic resonance image of the regulation object are input into the individualized navigation module, the functional connectivity network is generated to finalize regulatory targets. The position of stimulating electrodes and the magnitude of the stimulating current are determined according to the target to be regulated. The stimulating frequency is determined according to the EEG of the regulation object and then input into the AC stimulation module for regulation. During the regulation, the EEG acquired by the EEG acquisition module is input into the adaptive coupling module. The current of the AC stimulation module is regulated according to the EEG during the regulation to realize phase coupling with the waveform, so as to realize accurate closed-loop neural network regulation.

DETAILED DESCRIPTION

Figure 1:
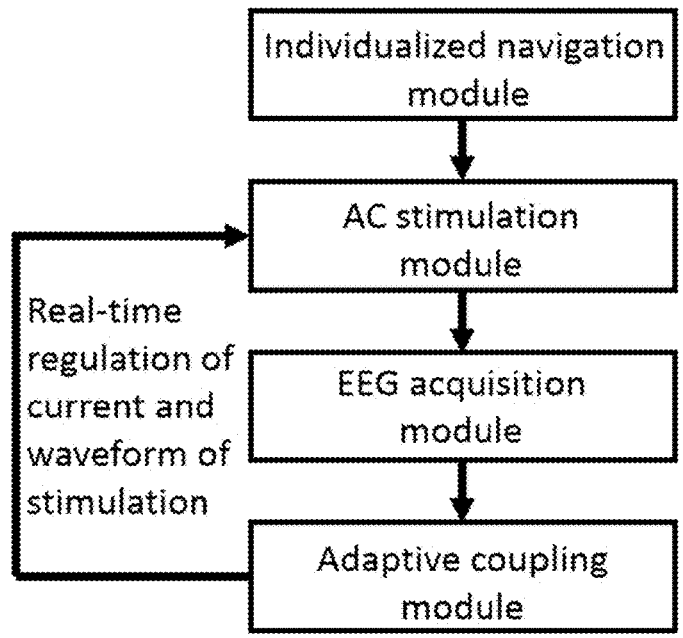
FIG. 1 shows the schematic diagram for the whole process of the regulation in this invention.

In order to make the objective, technical scheme and advantages of this invention clearer, this invention will be further detailed in combination with drawings and embodiments. It should be understood that the specific embodiments described are only used to explain this invention and are not used to limit this invention.

In the description of this invention, the orientations or positional relations indicated by such terms are based on the orientations or positional relations shown in drawings, are only used to facilitate the description of this invention and simplify the description, and are not used to indicate or imply that the device or element mentioned must have a specific orientation or should be constructed and operated in a specific orientation. Therefore, these orientations or positional relations should not be interpreted as limitations of this invention. In addition, unless otherwise expressly specified, the "multiple" in the description of this invention means two or more.

Embodiment 1

A closed-loop adaptive AC stimulation neural network regulation method, including the following steps:

S1: obtain the EEG image data of the regulation data, build head models and functional connectivity network, identify multiple targets for regulation and configure the current parameters of electrical stimulation output at each target according to the simulation and optimization results;

S2: electrically stimulate each target according to current parameters, measure the impedance in real time during the stimulation, and regulate the current output;

S3: perform EEG acquisition on each target after stimulation, and pre-process the data acquired;

S4: for the pre-processed data, use zero phase shift FIR filter for zero phase shift band filtering for specific band range according to the set time window; use the AR model for phase prediction for the filtered signal; carry out FFT power spectrum analysis to obtain the main frequency;

S5: regulate current parameters according to the predicted phase and main frequency, and repeat S2-S4 to realize the closed-loop neural network regulation.

In S1: build a 5-layer head model composed of the scalp, skull, cerebrospinal fluid, gray matter, white matter with MRI data and simnibs software; generate a func Specifically, in S1: compare the fMRI and EEG data with the Brain functional network and rhythm of normal people to obtain the abnormal region and rhythm that are the target of electrical stimulation and the frequency of regulation.

The position of the stimulating electrode and the magnitude of the stimulating current are determined by optimizing multiple HD-TACS: stimulate multiple targets with multiple electrodes to obtain the position of multiple stimulating electrodes by the least square method and based on the international 10/10 EEG system; perform parallel optimization by single electrode superposition method according to the superposition of electric field and the linear relation of current, after setting the common reference electrode, calculate the unit current of each electrode, realize the focus at the target position within the limited safe current range under the following evaluation conditions: the electric field in the target position in the region surrounded by the peripheral electrode is the largest; and the ratio of the electric field inside and outside the target is the smallest; change the current at the electrodes in each group to make the sum of the two conditions the minimum.

S3 includes: removing the noise and artifacts from the data acquired by ASR.

Embodiment 2

This invention relates to a closed-loop adaptive AC stimulation neural network regulation system, which is aimed at realizing the effective focused regulation of neural network rhythms and is composed of an individualized navigation module, AC stimulation module, EEG acquisition module and adaptive coupling module that are sequentially connected.

The Individualized navigation module builds of the head model and functional connectivity network with the image data of the regulation object, identifies the multiple targets to be regulated, determines the regulation frequency according to the EEG data of the regulation object, and optimizes the position of stimulating electrode and current by means of multiple HD-TACS to realize the multi-target electrical stimulation focused regulation;

The AC stimulation module obtains the electrode position and current parameters with the individualized navigation module, realizes the configuration of electrode parameters, and regulates the output current in real time combined with impedance detection to realize accurate electrical stimulation regulation while realizing limited protection;

The electrodes of this system have the function of two-way regulation and are provided on the head of the regulation object. The system can perform electrical stimulation via electrodes to regulate brain networks and can regulate the stimulation output parameters of devices by acquiring EEG from brain networks.

The EEG acquisition module acquires the EEG after electrical stimulation and pre-processes EEG.

The Adaptive coupling module analyzes and processes the EEG pre-processed by the EEG acquisition module, and then predicts the phase, re-sets the stimulating current and frequency of electrical stimulation and realizes the closed-loop neural network regulation.

Embodiment 3

FIG. 1 shows the whole process of regulation in this invention. After obtaining simulation targets and regulatory rhythms by integrating MRI, fMRI and EEG data by the individualized navigation module, the output current parameters and frequency parameters of electrical stimulation are configured according to simulation and optimization parameters. The AC stimulation module performs 3 s to 10 s of electrical stimulation according to the parameters output by the individualized navigation module. During the stimulation, the impedance was measured in real time to regulate the current output. Upon the completion of stimulation, the EEG acquisition module switches the electrode stimulation mode to acquisition mode and performs 3 s to 10 s of EEG acquisition and then pre-processing, after which the data are transmitted to the adaptive coupling module. When EEG data are processed, the phase for 3 s to 10 s is predicted. The current and frequency of electrical stimulation are re-set to further regulate electrical stimulation to realize the closed-loop neural network regulation.

Figure 2:
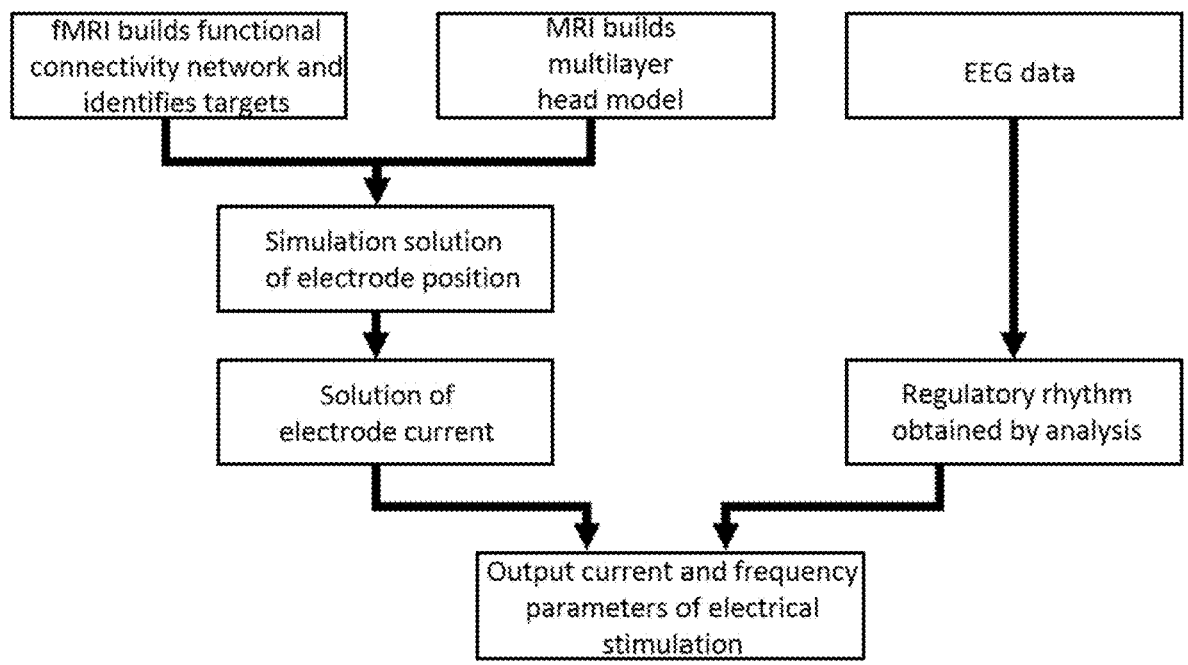
FIG. 2 shows the workflow diagram for the individualized navigation module in this invention.

As shown in FIG. 2, the flow of the individualized navigation module includes building the 5-layer head model composed of the scalp, skull, cerebrospinal fluid, gray matter and white matter by acquiring the MRI of the regulation object by simnibs software, generating functional connectivity network by acquiring the fMRI of the regulation object by GRETNA kit, and comparing the combined fMRI and EEG data with the brain functional network and rhythm of normal people to obtain the abnormal region and rhythm that are the target of electrical stimulation and the frequency of regulation. For the multiple stimulation targets obtained, the focused regulation of multi-target electrical stimulation is realized by optimizing multiple HD-TACS.

The method mentioned in the previous step is used to determine the position of stimulating electrodes and the magnitude of stimulating current to achieve the optimal stimulation effect. The traditional HD-TACS has a high focus effect and is composed of a total of 5 electrodes: four peripheral electrodes and one central electrode. It can focus the stimulation area within the peripheral area surrounded by 4 electrodes. The 5 electrodes are defined as a group. Multiple electrodes are used to stimulate the multiple targets obtained. For the center electrode of each electrode, the position of multiple stimulating electrodes is obtained by the least square method and based on the international 10/10 EEG system. After obtaining the position of stimulating electrodes, parallel optimization is performed by the single electrode superposition method according to the superposition of the electric field and the linear relation of current. After setting the common reference electrode, the unit current of each electrode is calculated first. The evaluation conditions are as follows: the electric field in the target position in the region surrounded by the peripheral electrode is the largest $a=\min(Ein)$; and the ratio of the electric field inside and outside the target is the smallest $b=\min(Eout/Ein)$; change the current at the electrodes in each group to make the sum of the two conditions the minimum $\min(a+b)$, so as to realize the focus at the target position.

Figure 3:
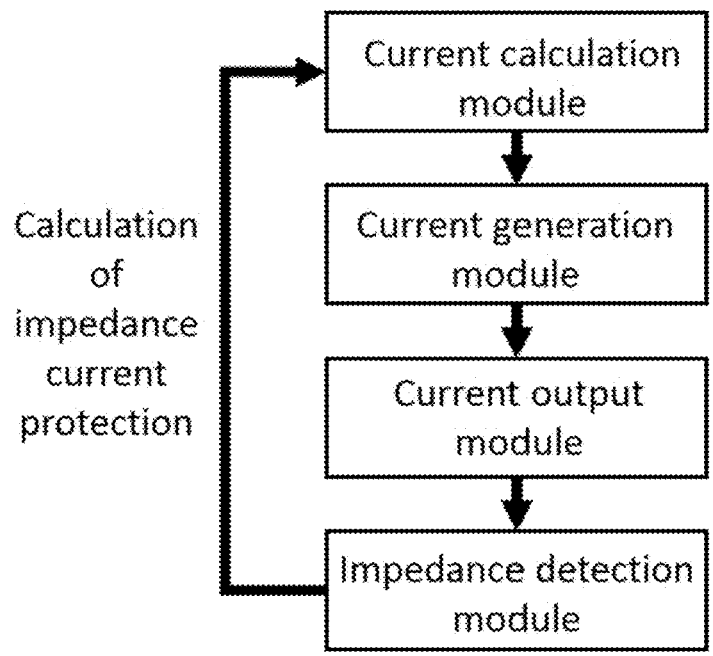
FIG. 3 shows the workflow diagram for the AC stimulation module in this invention.

As shown in FIG. 3, the AC stimulation module is composed of five sequentially connected parts, i.e. the current calculation part, current generation part, current output part, impedance detection part and EEG analysis part. The current calculation part is used to calculate the current of the electrode in each position according to the position information received, and perform limited protection of current in combination with impedance detection to avoid adverse effects on subjects due to overcurrent. The current generation part is used to generate the stimulating waveform of each stimulating electrode. This device adopts a series of high-precision electronic components. In combination with Holland current pump, it accurately outputs arbitrary stimulating waveform to the output module. The current output part is used to output the stimulating current and acquire EEG voltage. The output module has the function of limit-voltage circuit protection with a limited voltage of ±24V. The output module has 8 channels, each of which is composed of 5 electrodes, 4 for negative input and 1 for positive output. The impedance detection part is used to collect the current signal of each pair of electrodes and calculate the real-time impedance.

Figure 4:
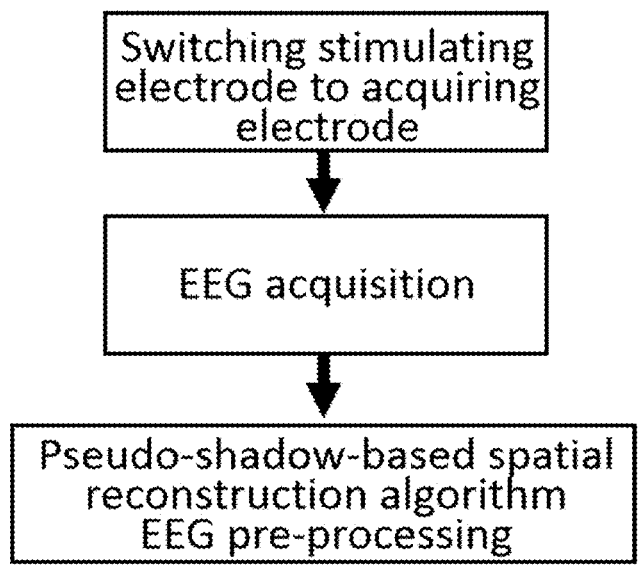
FIG. 4 shows the workflow diagram for the EEG acquisition module in this invention.

As shown in FIG. 4, the EEG acquisition module provides brainwave acquisition and pre-processing. After a period of electrical stimulation, the stimulating electrodes are switched to acquisition electrodes. Firstly, EEG is acquired with an 8-channel EEG acquisition device. Afterward, noise and artifacts are removed from the EEG data acquired by ASR to obtain the relatively pure EEG to realize the pre-processing of brain signals.

Figure 5:
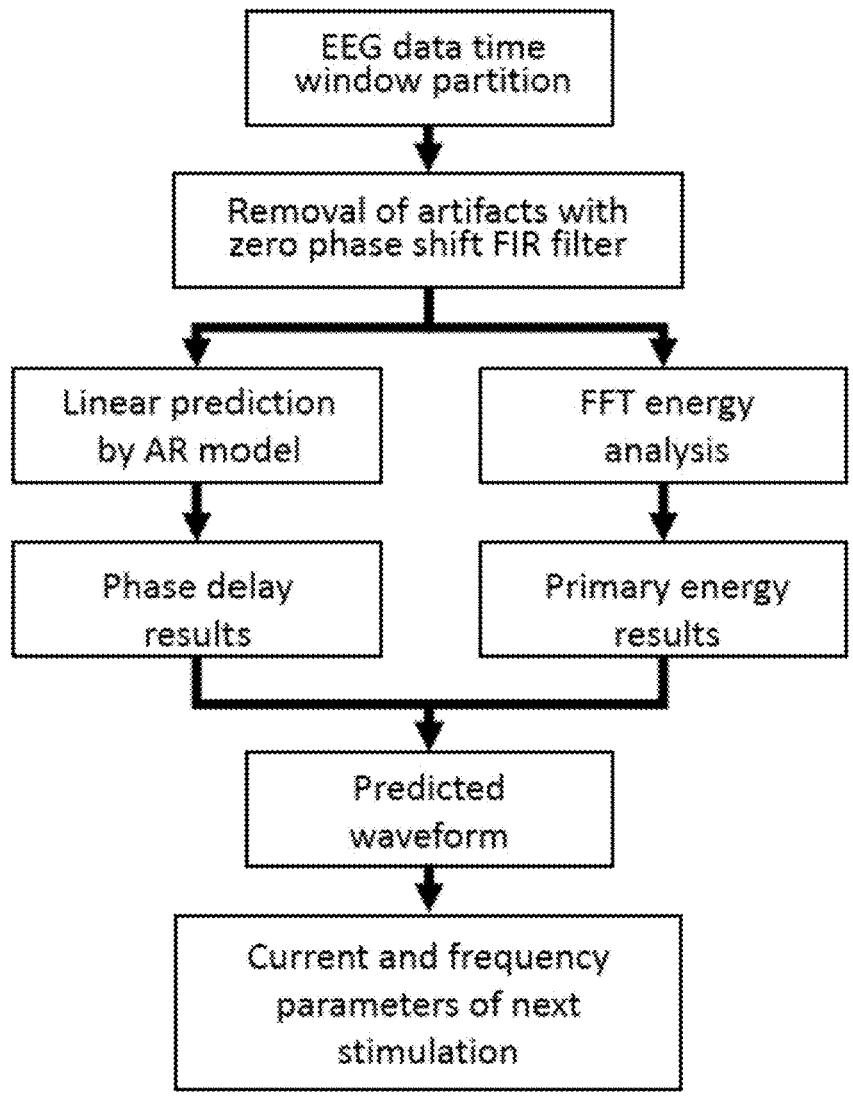
FIG. 5 shows the workflow diagram for the adaptive coupling module in this invention.

As shown in FIG. 5, the adaptive coupling module is mainly used to pre-process EEG and predict the phase and frequency and EEG. Firstly, the window partition of the original EEG acquired is performed according to the set time. Afterward, a zero phase shift FIR filter is used for zero phase shift band filtering for specific band ranges. The AR model is used for phase prediction for the filtered signal. Meanwhile, the FFT power spectrum is analyzed to obtain the main frequency. Finally, the AC stimulation module is controlled to output the obtained current and waveform according to the predicted phase and frequency. Thus neural regulation is performed to realize complete closed-loop regulation.

Figure 6:
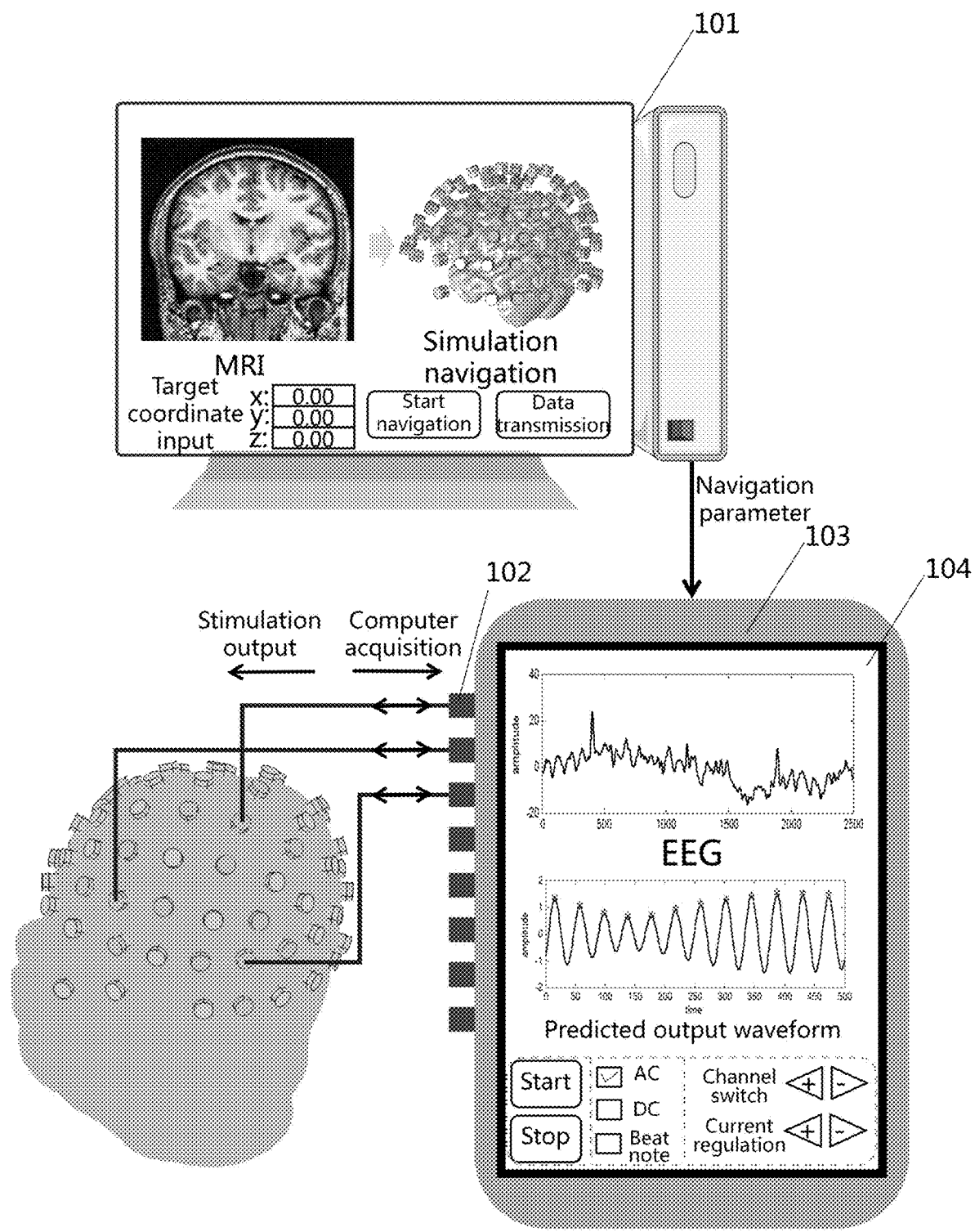
FIG. 6 shows the workflow diagram for the whole process of the regulation in this invention.

FIG. 6 shows the specific flow of regulation. Only the position of 3-channel stimulating (acquiring) electrodes is shown in the figure. Other channels are used as acquiring electrodes. The connection type is not displayed. Moreover, there is a difference in the position of different targets regulated. Other channels can also be used as stimulating electrodes. The specific operation procedures are as follows: after inputting the nuclear magnetic image of subjects and the positions of multiple stimulating targets into the individualized navigation module, the position of the optimized stimulating electrodes and the magnitude of current are obtained. After setting the time of acquisition and prediction, the data obtained are transmitted to the AC stimulation module. After clicking "start stimulation", 3 s to 10 s of EEG of subjects is acquired first. Afterward, prediction is performed to obtain the phase and frequency of the regulated stimulation. 3 S to 10 s of electrical stimulation output is performed. These procedures are repeated until reaching the set stimulation time.

As shown in FIG. 6, this invention is composed of an AC stimulation module, an EEG acquisition module and an adaptive coupling module. Not only AC stimulation can be performed, AC stimulation and differential frequency electrical stimulation can be realized to meet the needs of all regulatory modes.

The above-mentioned embodiments are only the optimal embodiments of this invention, and cannot be used to limit this invention. Any modification, equivalent replacement or improvement within the spirit and principle of this invention should be included in the protection scope of this invention.

What is claimed:
1. A closed-loop adaptive alternating current (AC) stimulation neural network regulation method, comprising:
   building, by an individualized navigation module, a head model and functional connectivity network with an image data of a regulation object;
   identifying multiple targets to be regulated;
   optimizing position of stimulating electrode and current by means of multiple high-density transcranial alternating current stimulation (HD-TACS), wherein the means of multiple HD-TACS comprises:
      stimulating the multiple targets with multiple electrodes to obtain the position of multiple stimulating electrodes by least square method and based on international 10/10 electroencephalogram (EEG) system;
   performing parallel optimization by single electrode superposition method according to superposition of electric field and linear relation of the current;
   setting a common reference electrode;
   calculating unit current of each electrode, locating a focus within a limited safe current range wherein the electric field at the focus is the largest; the ratio of the electric field inside and outside the multiple targets is the smallest; and the current at the multiple electrodes is the minimum;
by an AC stimulation module, stimulating the multiple targets based on the position of the stimulating electrode and the current, and regulating output current while performing impedance detection;
by an EEG acquisition module, performing EEG acquisition at the multiple targets and producing pre-processed EEG data;
by an adaptive coupling module, analyzing the pre-processed EEG data, predicting phase, resetting the current and frequency of electrical stimulation and realizing a closed-loop neural network regulation, wherein
the adaptive coupling module filters the pre-processed EEG data using a zero phase shift Finite Impulse Response filter according to a set time window; the adaptive coupling module uses an autoregressive model to predict the phase based on the filtered pre-processed EEG data; the adaptive coupling module performs a Fast Fourier Transform power spectrum analysis to obtain a main frequency; and the adaptive coupling module regulates the current according to the phase and the main frequency to realize the closed-loop neural network regulation.

2. A closed-loop adaptive AC stimulation neural network regulation system according to claim 1, wherein the multiple electrodes comprises four peripheral electrodes and one central electrode.

3. A closed-loop adaptive AC stimulation neural network regulation system according to claim 1, wherein the AC stimulation module comprises a current calculation module, a current generation module, a current output module and an impedance detection module, wherein the current calculation module calculates the current of each stimulating electrode according to the position of the stimulating electrode, the current generation module generates a stimulating waveform of each stimulating electrode based on the current, the current output module outputs electrical stimulation current and acquires EEG voltage, and the impedance detection module collects current signal of the stimulating electrodes and calculates a real-time impedance value.

4. A closed-loop adaptive AC stimulation neural network regulation system according to claim 3, wherein the current output comprises a limit-voltage protection circuit with a limited voltage of ±24V.

5. A closed-loop adaptive AC stimulation neural network regulation system according to claim 3, wherein the current output module has 8 channels, each of which comprises 5 electrodes, wherein 4 electrodes are configured for negative input and 1 electrode is configured for positive output.

* * * * *